United States Patent
Warnaar et al.

(10) Patent No.: US 7,632,496 B2
(45) Date of Patent: Dec. 15, 2009

(54) CO-ADMINISTRATION OF CG250 AND IL-2 OR IFN-α FOR TREATING CANCER SUCH AS RENAL CELL CARCINOMAS

(75) Inventors: Sven Ole Warnaar, Leiden (NL); Stefan Ullrich, Starnberg (DE)

(73) Assignee: Wilex AG, Munich (DE)

( * ) Notice: Subject to any disclaimer, the term of this patent is extended or adjusted under 35 U.S.C. 154(b) by 21 days.

(21) Appl. No.: 10/517,338

(22) PCT Filed: Jun. 23, 2003

(86) PCT No.: PCT/EP03/06591

§ 371 (c)(1), (2), (4) Date: Dec. 9, 2004

(87) PCT Pub. No.: WO2004/002526

PCT Pub. Date: Jan. 8, 2004

(65) Prior Publication Data

US 2005/0261178 A1 Nov. 24, 2005

Related U.S. Application Data

(60) Provisional application No. 60/392,311, filed on Jul. 1, 2002.

(51) Int. Cl.
A61K 39/395 (2006.01)

(52) U.S. Cl. .......................... 424/130.1; 514/2

(58) Field of Classification Search .................. None
See application file for complete search history.

(56) References Cited

U.S. PATENT DOCUMENTS

| | | | |
|---|---|---|---|
| 5,104,652 A | 4/1992 | Houghton et al. | |
| 5,772,997 A | 6/1998 | Hudziak et al. | |
| 5,830,452 A | 11/1998 | Bauer et al. | |

FOREIGN PATENT DOCUMENTS

| | | |
|---|---|---|
| WO | WO 93/18152 A1 | 9/1993 |
| WO | WO 97/41831 A1 | 11/1997 |

OTHER PUBLICATIONS

Busken, C et al, Digestive Disease Week Abstracts and Itinerary Planner, 2003.*
Vissers et al. (1999, Cancer Research 59:5554-5559).*
Uemura (1999, Brittish J. of Cancer 81(4):741-746).*
Bleumer et al., (Jan. 2002, European Urology Supplements, vol. 1, No. 1, pp. 112).*
Pavone (2001, Cancer Immunol. lmmunother. 50:82-86).*
Wiesenthal, Human Tumor Assay Journal, on-line (http://weisenthal.org/synergy1.htm, Aug. 5, 2008.*
Berenbaum, Clin exp Immunol, 1997, 28:1-18.*
Beck Joachim et al., "A Phase I/II trial with monoclonal antibody WX-G250 in combination with low dose interleukin-2 in metastatic renal cell carcinoma", Proceedings of the America Association for Cancer Research Annual, vol. 43, Mar. 2002, p. 910.
Bleumer I et al., "A phase II trial with monoclonal antibody WX-G250 in advanced renal cell carcinoma", European Urology Supplements, vol. 1, No. 1, Jan. 2002, p. 112.
Liu Zhanqi et al., "Anti-renal cell carcinoma chimeric antibody G250: Cytokine enhancement of in vitro antibody-dependent cellular cytotoxicity", Cancer Immunology Immunotherapy, vol. 51, No. 3, May 2002, pp. 171-177.
Van Dijk J. et al., "Therapeutic effects of monoclonal antibody G250, interferons and tumor necrosis factor, in mice with renal-cell carcinoma xenografts", International Journal of Cancer, vol. 56, No. 2, 1994, pp. 262-268.
Varga Z et al., "A prospective open-label single-arm phase II study of chimeric monoclonal antibody cG250 in advanced renal cell carcinoma patients", Folia Biologica, vol. 49, No. 2, 2003, pp. 74-77.
Bleumer Ivar et al., "A phase I/II trial with chimeric monoclonal antibody WX-G250 in combination with low-dose interleukin-2 for patients with metastatic renal cell carcinoma", Journal of Urology, vol. 169, No. 4 Supplement, Apr. 2003, p. 261.
Hank et al., "Augmentation of Antibody Dependent Cell Mediated Cytotoxicity following in Vivo Therapy with Recombinant Interleukin 2", Cancer Research, 50, Sep. 1, 1990, p. 5234-5239.
Uemura et al, "Effects of MAbG250 and Anti-Idiotye Antibody Based Immunotherapy in Renal Cell Carcinoma", Biotherapy, pp. 400-403, 11 (3) : Mar. 1997.

(Continued)

Primary Examiner—Misook Yu
Assistant Examiner—Mark Halvorson
(74) Attorney, Agent, or Firm—Rothwell, Figg, Ernst & Manbeck, P.C.

(57) ABSTRACT

A method for enhancing the therapeutic effect of cytokine treatment is disclosed. More specifically the present invention relates to a method for administering to a tumor patient a therapeutic dose of cytokine in combination with antibodies directed against the tumor associated antigen carbonic anhydrase IX (CAIX/G250/MN). The improved treatment method is characterized in a significantly reduced cytokine-related toxicity combined with potentiated effectiveness of anti-G250 antibody alone, resulting in a positive therapeutic response with respect to that observed with single anti-tumor agents alone.

11 Claims, No Drawings

OTHER PUBLICATIONS

Christianne Buskens et al., "Adenocarcinomas of the Gastroesophageal junction: a comparative study of the gastric cardia and the esophagus with respect to cycloxygenase-2 expression", Digestive Disease Week Abstracts and Itinerary Planner, vol. 2003, 2003, page Abstract No. 850.

Kim A. Margolin, "Interleukin-2 in the Treatment of Renal Cancer", Seminars in Oncology, vol. 27, No. 2, Apr. 2002, pp. 194-203.

Peter F.A. Mulders et al., "The Role of Adjuvant Immunotherapy in Renal Cell Carcinoma", Current Urology Reports, 2002, vol. 3 pp. 44-49.

Kendall A. Smith, "Lowest Dose Interleukin-2 Immunotherapy", Blood, vol. 81, No. 6, Mar. 15, 1993, pp. 1414-1423.

Paul M. Sondel et al., "Clinical and Immunological Effects of Recombinant Interleukin 2 Given by Repetitive Weekly Cycles to Patients with Cancer", Cancer Research 48, May 1, 1988, pp. 2561-2567.

Jeff A. Sosman et al., "Repetitive Weekly Cycles of Interleukin-2. II. Clinical and Immunological Effects of Dose, Schedule, and Addition of Indomethacin", Journal of the National Cancer Institute vol. 80, No. 18, Nov. 16, 1998, pp. 1451-1461.

R. C. Stein et al., "The clinical effects of prolonged treatment of patients with advanced cancer with lose-dose subcutaneous interleukin 2", Br. J. Cancer 63, 1991, pp. 275-278.

J. R. Turner et al., "MN antigen expression in normal, preneoplastic, and neoplastic esophagus: a clinicopathological study of a new cancer-associated biomarker", Hum Pathol Jun. 1997; 28(6):740-4, PubMed Abstract.

M.L. Nasi et al., "Treatment (tx) with daily low-dose subcutaneous (sc) interleukin-2 (IL-2) followed by monoclonal antibody R24 against GD3 ganglioside in patients (pts) with metastatic melanoma (MM)", http://www.asco.org/prof/me/html/abstracts/ms/m_1770.htm, 1997.

Joost L. M. Vissers et al., "The Renal Cell Carcinoma-associated Antigen G250 Encodes a Human Leukocyte Antigen (HLA)-A2.1-restricted Epitope Recognized by Cytotoxic T Lymphocytes", Cancer Research 59, Nov. 1, 1999, pp. 5554-5559.

* cited by examiner

CO-ADMINISTRATION OF CG250 AND IL-2 OR IFN-α FOR TREATING CANCER SUCH AS RENAL CELL CARCINOMAS

CROSS REFERENCE TO RELATED APPLICATION

This application is a 35 USC § 371 National Phase Entry Application from PCT/EP03/06591, filed Jun. 23, 2003, and designating the U.S., which claims priority from U.S. Provisional 60/392,311 filed Jul. 1, 2002.

The invention relates to a method for the treatment of malignant disorders, particularly renal cell carcinoma (RCC), comprising the coadministration of low-dose cytokine, particularly IL-2 or IFN-α, and an antitumor antibody.

It is estimated that 30,000 new cases of renal cell carcinoma (RCC) were diagnosed in the United States in 1999, with 11,900 deaths resulting from the disease (1). Estimates of new cases that have overt metastatic disease at the time of diagnosis range from 25% to 40% (2;3). Prognosis for these patients is bleak, with a median survival of 10 months. For the remaining cases in which the disease appears to be localized, the treatment of choice is radical nephrectomy. However, one third of these patients will later manifest metastatic disease and ultimately die from their cancer.

To date chemotherapy has not demonstrated sufficient antitumor activity to prolong the survival of patients with metastatic disease (4;5). Single agent or multiple agent chemotherapy has not demonstrated a response rate greater than 10-15%. Due to less than satisfactory responses to chemotherapy and surgery, and to the indirect evidence that host immune mechanisms play a significant role in the natural history of RCC, there is a continued exploration of immunotherapy in this disease (6-8). Interferon-alpha (IFN-α) and interleukin-2 (IL-2) have indeed shown anti-tumor activity in approx. 20% of patients (9-13), but this was often associated with severe toxicity.

Interleukin-2 (IL-2) is an immune system stimulating agent that can enhance proliferation and activation of T cells, NK cells and LAK cells and can induce the secretion of a variety of cytokines including IL-6 and interferon alpha (IFN-α) and gamma (IFN-γ). Initial administration of IL-2 causes a transient disappearance of lymphocytes from the vascular compartment with a rebound after 24-48 hrs. After prolonged administration an expansion of various types of white blood cells is seen. IL-2 has been extensively investigated as an immune therapeutic for cancer and was shown to have activity against melanoma and renal cancer (6,8). High dose IL-2 therapy has been approved by FDA for the treatment of advanced renal cell carcinoma. The dosing scheme consists of an intravenous bolus of 0.6-0.7 MIU/kg every 8 hrs, repeated until further therapy is limited by toxicity (18). A treatment course consists of two cycles of therapy separated by 7-10 days. In each cycle patients may receive 10-14 doses of IL-2. The overall response rate is 15% with 5% complete responses.

There is considerable toxicity related to this high dose IL-2 treatment, requiring uptake in an intensive care unit. A sepsis-like syndrome with hypotension requiring pressor support as well as a systemic vascular leakage leading to respiratory distress can occur. Other toxicities/side effects are cardiac arrhythmia, fluid retention, fever, headache and mental confusion, elevation of liver enzymes, nausea and vomiting, thrombocytopenia, hyper/hypothyreoidism, and pruritus (18). Due to the high toxicity profile alternative dosing schemes have been developed, such as low dose iv and sc treatment, aiming at reducing toxicity while retaining efficacy. In general it can be stated that these low dose treatments indeed are far less toxic (19-22). Generally, this low-dose IL-2 treatments, however, do not show any substantial efficacy.

The antibody G250 recognizes the tumor-associated antigen carbonic anhydrase IX (CAIX/G250/MN), present on more than 75% of renal cancers. The reactivity with normal tissues is restricted to the gastric epithelium and the biliary ducts in the liver (14;15). Phase I/II trial of the murine G250 antibody with $^{131}$I labeling for radioimmunotherapy has been completed and the results have been published (16). A chimeric G250 antibody constructed from a mouse Fv region with a human IgG1 kappa Fc region (15) has been shown to be equivalent to the murine G250 antibody in competitive combinding assays. The chimeric antibody was labeled with $^{131}$I and used for diagnostic study in RCC patients (17).

The administration of a combination of cytokines and therapeutic antibodies has been described (24, 25, 26, 27, 28; U.S. Pat. No. 5,104,652 and WO 01/87336. There have been different schemes for the administration of antibody and cytokine combinations, which, however, have generally not shown the desired synergic effects and finally remained unsuccessful. Most of the IL-2 treatment protocols comprise an intermittent short-term administration of IL-2 in order to reach a reduction of the side effects.

Liu et al. (Cancer Immunol Immunother 51 (2002), 171-177) describe a cytokine enhancement of ADCC by administration of chimeric G250 antibody in vitro. According to the authors, these results suggest that a combination immunotherapy of chimeric G250 antibody with cytokines such as IL-2 might show promise in the treatment of RCC.

An abstract of Beck et al., Proceedings of the American Association for Cancer Research, Vol. 43, (Mar. 2002) describes a phase I/II trial with monoclonal antibody G250 in combination with low dose IL-2 in metastatic RCC. In phase I, patients received G250 once weekly i.v. and IL-2 s.c. according to an alternating low dose and periodic pulsing treatment scheme over 6 weeks (1.8 MIU or 5.4 MIU IL-2 per day, single dose). During phase II, six patients continued to receive treatment for another 6 weeks and nine additional patients were enrolled for a 12-week treatment. While the treatment was tolerated well, 4 of 14 patients showed stabilization of initially progressive disease. One of these four showed a partial remission when seen for the follow up in week 34. An additional patient had a partial remission first observed in week 16, this response was last confirmed in week 34.

The object underlying the present invention was to provide a treatment protocol for coadministering an anti-tumor antibody and a low dose cytokine which is more efficient than previous protocols without causing substantive side effects.

According to the present invention, a novel method for the treatment of a malignant disorder is provided, comprising coadministering an anti-tumor antibody and a cytokine, wherein the cytokine is administered continuously or repeatedly, preferably daily in a low dose form.

A further embodiment of the present invention relates to a method for the treatment of a malignant disorder, comprising:

a) first treatment stage comprising administering a low-dose cytokine, preferably a continuous or repeated administration of a low-dose cytokine, and b) a second treatment stage comprising coadministering an anti-tumor antibody and a low-dose cytokine, wherein the cytokine is preferably administered continuously or repeatedly.

According to the present invention, the cytokine is administered in a low-dose form, wherein the administration preferably occurs continuously or repeatedly over the whole therapy interval. The administration is preferably daily each second day, and/or three times a week. By means of this continuous/repeated low-dose administration, the cytokine level is sufficiently high to increase the activity of the anti-tumor antibody, e.g. by increasing ADCC and/or to activate the immune system of the patient, e.g. the NK cells without causing substantial side effects, particularly cytokine-related toxicity. Compared to an administration of the anti-tumor antibody or the cytokine alone, the therapeutic efficacy of the combined administration is increased by more than 15%.

The administration of "low-dose cytokine" according to the present invention means that the cytokine is administered in a dose which is pharmaceutically effective in improving the efficacy of an antibody therapy in the substantial absence of toxic side effects, e.g. in the substantial absence of grade 3 or higher of National Cancer Institute (NCI) Common Toxicity Criteria (CTC) Version 2.0, April 1999, more preferably in the substantial absence of grade 2 or higher and most preferably in the substantial absence of grade 1 or higher.

The cytokine is preferably selected from the group consisting of interleukins, e.g. IL-2,3,4,5,6,7,8,9,10,11,12,13,14 and 15, interferons e.g. IFN-α, IFN-β and IFN-γ, TNF-α, TNF-β, nerve growth factor (NGF), ligands of CD 40, FAS, CD 27 and CD 30, macrophage-inhibiting protein, Rantes, active fragments and pharmaceutically acceptable analogues and derivatives thereof and mixtures thereof. More preferably, the cytokine is selected from IL-2 and IFN-α. A preferred dosage of IL-2 in the range of 1 MIU to 10 MIU daily, particularly in the range of 1.5 MIU to 6 MIU daily. The preferred dosage of IFN-α is 1 to 10 MIU three times a week, particularly in the range of 1 to 4 MIU three times a week.

The cytokine dose may be constant during the whole treatment. Alternatively, the dose may be a variable dose, particularly in the second treatment stage of a two-stage protocol, i.e. the dose may be altered during the treatment between a first low dose and a second low dose, wherein the second low dose may be up to five times higher than the first low dose. For example, the first low dose may be given in the first week of treatment, e.g. in the second treatment stage of a two-stage protocol, and in the second week, the first and second dose are given alternatively. In the third week, the administration is as in the first week, the fourth week, the administration is as in the second week and so on.

The cytokine may be administered subcutaneously or intravenously or in any combination thereof. The preferred administration is subcutaneously.

The second active ingredient of the therapy according to the present invention is an anti-tumor antibody. The term "anti-tumor antibody" according to the present invention relates to any antibody which has efficacy against a malignant disorder, particularly renal cell carcinoma. Preferably, the antitumor antibody is directed against a so-called tumor antigen, i.e. an antigen, particularly a polypeptide or a carbohydrate structure which is associated with a malignant disorder such as specified above.

More preferably the antitumor antibody is selected from antibodies directed against the MN (G250) antigen. Antibodies against the MN antigen are for example described in EP-B-0 637 336. Especially preferable, the antitumor antibody is a chimeric or humanized G250 antibody or a fragment thereof. These antibodies may be produced by methods as described in PCT/EP/02/01282 and PCT/EP/02/01283.

The antitumor antibody is preferably administered intravenously, e.g. by infusion or intravenous injection. The administration of the antitumor antibody is preferably in intervals of from 5-20 days, e.g. in intervals of about 1 week.

The whole treatment protocol of the invention preferably comprises time interval of from 50-200 days. If the treatment comprises a two-stage treatment, the first treatment stage preferably comprises 5-20 days, e.g. about one week and the second treatment stage preferably comprises 5-200 days, e.g. about 70-120 days.

Furthermore, the invention should be explained by the following examples.

EXAMPLE 1

Clinical Trial Comprising Coadministration of Chimeric G250 Antibody (cG250) and IL-2

1.1 Endpoint Criteria
   Primary Endpoints
   Toxicity
   Objective tumor response
   Secondary Endpoints
   ADCC
   HACA
   Time to progression
   Overall survival 1.2 Design A prospective, open label, single arm, non-randomized phase I/II multicenter trial was carried out in patients with advanced renal cell cancer. In the phase I part of the study the first 6 patients received cG250 once weekly intravenously and IL-2 subcutaneously according to an alternating low dose (daily) and periodic pulsing treatment scheme for 6 weeks. After it was shown that the drug-related toxicity was acceptable according to defined criteria these 6 patients were treated for another 6 weeks for a total of 12 weeks and an additional 9 patients (start of the phase II part) were enrolled for a 12 weeks treatment. Patients showing objective response (CR, PR) or stable disease were offered an additional treatment cycle of 6 weeks.

The data base closure for the final analysis of all parameters except for time of progression was the evaluation at week 22 for all patients. Further, the results of the long-term follow up for defining the time to progression of the objective responders and the stable disease patients were evaluated.

1.3 Study Treatment, Dosage and Dosage Regimen/Administration cG250 was administered according to the treatment schedule in Table 1. Per dose 20 mg of the chimeric monoclonal antibody cG250 were given once a week (plus or minus two days) by intravenous infusion in 50-100 ml of normal saline for 11 consecutive weeks in total, preceded by a week of IL-2 alone. The infusion was administered over a period of 30 minutes.

IL-2 was administered subcutaneously according to the treatment schedule in Table 1. Subjects received or self-administered at home a single daily injection of commercially available recombinant human IL-2 for 12 consecutive weeks. Starting in week 1, patients received a single dose of 1.8 MIU sc IL-2 daily. In week 2 on day 1 the same amount of IL-2 was given preceded by cG250. The remaining days of week 2 patient received 1.8 MIU sc per day. In week 3 from day 1 to 3, patients received sc IL-2 pulsing with 5.4 MIU per day. On the remaining days IL-2 was given at 1.8 MIU. The IL-2 treatment of week 3 was repeated in week 5, 7, 9, and 11, the scheme of week 2 in week 4, 6, 8, 10, and 12.

In general the IL-2 injections were made early in the morning by the patient at home. Only on days of cG250 administration this injection was delayed until the patient was in the outpatient clinic. On the day of G250 application patients received IL-2 (irrespective of dose) one hour after the G250 therapy.

1.4 Test Schedule and Procedures/Study Flow Chart

The study procedures are described in detail in this section. A general overview of the tests and procedures of this protocol is given in the G250/IL-2 application scheme (Table 1).

Patients were closely monitored for safety reasons during the treatment period by weekly controls of vital signs, assessment of toxicity, Performance Status and laboratory tests, eg CBC, blood chemistry and radiological tests, if necessary. All blood drawings were performed before the administration of IL-2 and G250, respectively. The total volume of the blood drawings per patient in 5 months were about 300 ml.

The investigations/evaluations that were performed are listed in the following Table 1:

TABLE 1 cG250/IL-2 application scheme

| | cG250 | IL-2 |
|---|---|---|
| Week 1 | None | Day 1-7: 1.8 MIU per day single dose |
| Week 2 | Day 1: 20 mg single dose | Day 1-7: 1.8 MIU per day |
| Week 3 | " | Day 1-3: 5.4 MIU per day (pulsing scheme) Day 4-7: 1.8 MIU per day |
| Week 4 | " | As week 2 |
| Week 5 | " | As week 3 |
| Week 6 | " | As week 2 |
| Week 7 | " | As week 3 |
| Week 8 | " | As week 2 |
| Week 9 | " | As week 3 |
| Week 10 | " | As week 2 |
| Week 11 | " | As week 3 |
| Week 12 | " | As week 2 | cG250: iv infusion once weekly, given on day 1 of each week, outpatient clinic
IL-2: sc injection seven days/week, day 1 should be Monday or Tuesday, outpatient clinic and at home 1.5 Toxicity Classification Allergic reactions: Patients were removed from study for any grade $\geq 2$ allergic toxicity according to NCI CTC toxicity scale.

Fever: Patients with >39° C. fever (grade 2), but without allergic symptoms on the day of scheduled cG250 infusion did not receive cG250 until fever had dropped below 38° C. (grade 0). If fever did not drop in 2 days, the cG250 infusion was cancelled and treatment was resumed on the next scheduled G250 infusion date.

The sc injections of IL-2 were on days with fever >39° C. The daily IL-2 injections were cancelled until fever has dropped below 38° C. In case the use of 500 mg paracetamol did not decrease the temperature below 38° C., the injection was suspended until the temperature is below 38° C. again.

Pain, itching, erythema, swelling, inflammation, phlebitis and ulceration at the site of injection was considered as "local site reaction" according to the NCI CTC criteria; urticaria was diagnosed as part of "allergic reaction/hypersensitivity".

1.6 Assessment of Efficacy 1.6.1 Efficacy Parameters

The objective response of the tumor was the main parameter of efficacy. The tumor evaluation was performed based on the WHO Tumor Evaluation Guidelines with 1) minimum size requirements for measurable target lesions and 2) tumor masses with clearly defined bi-dimensional measurements.

The tumor measurements for target lesions were performed with CT-scan or MRI scan. For all indicator lesions the minimum size of the largest tumor diameter was 1.0 cm.

All measurable lesions $\geq 1.0$ cm up to a maximum of 5 lesions per organ and 10 lesions in total, representative of all involved organs, were identified as target lesions and recorded and measured at baseline.

1.6.2 Methods of Assessments (eg Tumor Response, Specific Tests)

The tumor assessment was based on contrast medium-enhanced spiral computer-tomography (CT) or magnetic resonance imaging (MRI). The same procedures were used throughout the study. All measurements were recorded in metric notation, using a ruler or calipers. All baseline evaluations were performed as closely as possible to the beginning of treatment and not more than 4 weeks before the beginning of treatment.

Tumor responses were evaluated according to the WHO criteria as follows: Complete response (CR): The disappearance of all known disease determined by two evaluations not less than four weeks apart.

Partial response (PR): 50% or more decrease in the sum of products of largest and perpendicular diameters of the lesions which have been measured to determine the effect of therapy by two evaluations not less than four weeks apart. In addition there can be no appearance of new lesions or progression of any lesion.

No change (NC)=Stable disease (SD): A greater than 50% decrease in total tumor size can not be established nor has a 25% increase in the size of one or more measurable lesions been demonstrated.

Progressing disease (PD): a 25% or more increase in the size of one or more measurable lesions, or the appearance of new lesions.

1.6.3 Timing of Tumor Evaluations

Tumor evaluations were performed before study entry, at week 16 and 22 and for drop-outs at time of drop-out. The assessment in week 22 did serve to confirm the radiologic result seen in week 16.

An effort was made to follow up all patients who are not progressing during their courses of treatment by performing CTs every 3 months after end of cG250 treatment. This served to assess the duration of the objective response or stable disease.

1.6.4 ADCC Assay

The antibody-dependent cell-mediated cytotoxicity (ADCC) of isolated peripheral-blood mononuclear cells (PBMC) from patients was analyzed using a $^{51}$Cr release assay, according to Lamers et al. (29). Target cells were the SKRC MW1-cl4 (G250 antigen overexpressing RCC cell line). Controls were SKRC PBJ-cl1 (G250 antigen negative RCC cell line) and P815 (positive control with anti-P815 serum). After incubation with G250 and serial dilutions of PBMC of the patients the $^{51}$Cr released by lysed target cells was measured in the supernatant. The weighted mean of specific lysis of target cells was calculated.

1.7 Statistics 1.7.1 Methods/Analysis

The study was based on a sequential enrollment of two groups of patients with a maximum of 30 evaluable patients enrolled. After enrolling 15 patients (stage 1) the study was continued enrolling the second group of 15 patients.

At the maximum enrollment number of 30 patients the trial was powered at 81% to detect an objective response rate of 15% against an assumed spontaneous response rate of 5%.

This trial design was chosen to minimize the expected enrollment of patients under objective and spontaneous response rates while maximizing the chances of early stopping at the interim analysis. The method of calculation was the Sequential Probability Ratio Test modified according to Wald (30, 31).

The study size was based on α≦0.05 and 1-β≦0.80 to detect a difference between a spontaneous response rate of 5% versus an underlying true response rate of 15%.

1.8 Results

According to an internationally accepted definition (32), an objective response or disease stabilization for approximately at least six months after the disease being progressive at study entry is generally accepted as a "clinical benefit".

In the present study, approximately 30% of patients exhibited an objective response or a disease stabilization for 22 weeks or longer and therefore the above treatment schedule represents a "clinical benefit" for the treated patient group. A clinical benefit to such an extent has not been observed for this very problematic patient group (metastatic RCC patients, often in the terminal stage of the disease).

Further, the treatment is safe. The combination treatment of i.v. adminstered cG250 and sc administered IL-2 was well tolerated. No serious adverse events against cG250 were observed. Moderate adverse events typical for IL-2 treatment (and in most cases tolerable due to the low dose administration) and no allergic reactions and no human anti-chimeric antibody (HACA) reactions were observed.

EXAMPLE 2

Clinical Trial Comprising Coadministration of Chimeric G250 Antibody (cG250) and IFN-α

The clinical trial was carried out as described in Example 1 except for the alterations in the administration protocol as shown in Table 2:

TABLE 2 cG250/IFN-α application scheme

| | cG250 | IFN-α |
|---|---|---|
| Week 1 | None | Day 1/3/5: 3 MIU single dose each |
| Week 2-12 | Day 1: 20 mg single dose | Day 1/3/5: 3 MIU single dose each |
| For all patients with approved extension of treatment | | |
| Week 17-22 | Day 1: 20 mg single dose | Day 1/3/5: 3 MIU single dose each | cG250: iv infusion once weekly, given on day 1 of each week, outpatient clinic
IFN-α: sc injection 3 times per week, outpatient clinic and at home The combination treatment of cG250 i.v. and IFN-α is s.c., was well tolerated. No serious adverse effects, related to cG250, were observed.

Only moderate adverse events, typical for IFN-α treatment were found. These adverse events were well tolerable due to the low dose administration protocol. Further, no allergic reactions and no HACA-reactions were observed.

Preliminary results show the presence of a clinical benefit for the treated patient group.

REFERENCES

1. Landis S H et al. Cancer statistics, 1999. Cancer Journal for Clinicians 1999, 49:8-31.
2. DeKernion J B et al. The natural history of metastatic renal cell carcinoma: a computer analysis. Journal of Urology 1978; 120:148-152.
3. Waters W B et al. Aggressive surgical approach to renal cell carcinoma: review of 130 cases. Journal of Urology 1979; 122:306-309.
4. Yagoda A et al. Chemotherapy for advanced renal-cell carcinoma: 1983-1993. Seminars in Oncology 1995; 22:42-60.
5. De Kernion J B et al. Selection of initial therapy for renal cell carcinoma. Cancer 1987; 60:539-546.
6. Bukowski R M et al. Phase II trial of high-dose intermittent interleukin-2 in metastatic renal cell carcinoma: a Southwest Oncology Group study. Journal of the National Cancer Institute 1990; 82:143-146.
7. Debruyne F M et al. New prospects in the management of metastatic renal cell carcinoma. Experimental and clinical data. Progress in Clinical & Biological Research 1990; 350:243-255.
8. Rosenberg S A. Clinical immunotherapy studies in the Surgery Branch of the U.S. National Cancer Institute: brief review. Cancer Treatment Reviews 1989; 16 Suppl A: 115-121.
9. Hercend T et al. Immunotherapy with lymphokine-activated natural killer cells and recombinant interleukin-2: a feasibility trial in metastatic renal cell carcinoma. Journal of Biological Response Modifiers 1990; 9:546-555.
10. Kelloumpu-Lehtinen P et al. Recombinant interferon-alpha 2a and vinblastine in advanced renal cell cancer: a clinical phase I-II study. Journal of Biological Response Modifiers 1990; 9:439-444.
11. Neidhart J A et al. Vinblastine fails to improve response of renal cancer to interferon (-n1: high response rate in patients with pulmonary metastases. Journal of Clinical Oncology 1991; 9:832-837.
12. Otto U et al. Recombinant alpha-2 or gamma interferon in the treatment of metastatic renal cell carcinoma: results of two phase II/III trials. Progress in Clinical & Biological Research 1990; 350:275-282.
13. Quesada J R et al. Recombinant interferon (2 and (in combination as treatment for metastatic renal cell carcinoma. Journal of Biological Response Modifiers 1988; 7:234-239.
14. Oosterwijk E et al. Antibody localization in human renal cell carcinoma: a phase I study of monoclonal antibody G250. Journal of Clinical Oncology 1993; 11:738-750.
15. Oosterwijk E et al. Monoclonal antibody G250 recognizes a determinant present in renal-cell carcinoma and absent from normal kidney. International Journal of Cancer 1986; 38:489-494.
16. Divgi C R et al. Phase I/II radioimmunotherapy with iodine-131 labeled monoclonal antibody (mAb) in metastatic renal carcinoma. Clin Cancer Res 1998; 4:2729-2739.
17. Steffens M G et al. Targeting of renal cell carcinoma with iodine-131-labeled chimeric monoclonal antibody G250. Journal of Clinical Oncology 1997; 15:1529-1537.
18. Parkinson D R et al. High-dose Interleukin-2 in the therapy of metastatic renal-cell carcinoma. Seminars in Oncology 1995; 22:61-66.

19. Stadler W M et al. Low-dose Interleukin-2 in the treatment of metastatic renal-cell carcinoma. Seminars in Oncology 1995; 22: 67-73.
20. Lissoni P et al. Second line therapy with low-dose subcutaneous interleukin-2 alone in advanced renal cancer patients resistant to interferon-alpha. Eur.J.Cancer 1992; 28: 92-96.
21. Meropol N J et al. Daily subcutaneous injection of low-dose interleukin-2 expands natural killer cells in vivo without significant toxicity. Clin. Canc. Res. 1996; 2: 669-677.
22. Meropol N J. et al. Evaluation of natural killer cell expansion and activation in vivo with daily subcutaneous low-dose interleukin-2 plus periodic intermediate-dose pulsing. Canc. Immunol Immunother 1998; 46: 318-326.
23. Surfus J E et al. Anti-renal-cell carcinoma chimeric antibody G250 facilitates antibody-dependent cellular cytotoxicity with in vitro and in vivo interleukin-2-activated effectors. Journal of Immunotherapy with Emphasis on Tumor Immunology 1996; 19:184-191.
24. Ziegler L D et al. Phase I trial of murine monoclonal antibody L6 in combination with subcutaneous interleukin-2 in patients with advanced carcinoma of the breast, colorectum and lung. J.Clin Oncol 1992; 10: 1470-1478.
25. Soiffer R J et al. Administration of R24 monoclonal antibody and low-dose interleukin-2 for malignant melanoma. Clin Canc Res 1997; 3: 17-24.
26. Vlasveld L T et al. Treatment of low-grade non-Hodgkin's lymphoma with continuous infusion of low-dose recombinant interleukin-2 in combination with the B-cell-specific monoclonal antibody CLB-CD19. Canc Immunol Immunother 1995; 40:37-47.
27. Riethmüller et al. Randomized trial of monoclonal antibody for adjuvant therapy of resected Dukes'C colorectal carcinoma. Lancet 1994; 343: 1177-1183.
28. Albertini M R et al. Phase IB trial of chimeric antidisialoganglioside antibody plus interleukin 2 for melanoma. Clin Canc Res 1997; 3: 1277-1288.
29. Lamers C. H. J. et al. Exogenous Interleukin 2 recruits in vitro lymphokine activated killer activity by in vivo activated lymphocytes. Canc Res 1991; 51: 2324-2328.
30. Wald A and Wolfowitz J. Optimum character of the sequential probability ratio test. Ann. Math. Stat. 1948. Vol 19, 326-339.
31. Wald A and Wolfowitz J. Bayes solutions of sequential decision problems. Ann. Math. Stat. 1950. Vol 21, 82-99.
32. Motzer R J et al., J. Clin. Oncol. 2002; 20, 302-306

The invention claimed is:

1. A method for the treatment of renal cell cancer comprising co-administering an anti-tumor antibody directed against the MN antigen, wherein said antitumor antibody is a chimeric or humanized G250 antibody or an antigen binding fragment thereof and a cytokine to a subject in need thereof, wherein the cytokine is IFN-α and is administered continuously or repeatedly in a low-dose form, wherein the low-dose cytokine comprises a dose which is pharmaceutically effective in the absence of NIC CTC toxicity grade 3 or higher, and wherein said G250 antibody or fragment thereof and said IFN-α are the only active ingredients which are administered.

2. A method for the treatment of renal cell cancer comprising co-administering an anti-tumor antibody G250 directed against the MN antigen and cytokine to a subject in need thereof, wherein the cytokine consists of interferon-α and the method comprises:
    (a) a first treatment stage comprising administering a low-dose interferon-α, and
    (b) a second treatment stage comprising co-administering the anti-tumor antibody G250 and a low-dose interferon-α as the only active ingredients, and wherein the low-dose interferon-α comprises a dose which is pharmaceutically effective in the absence of NIC CTC toxicity grade 3 or higher.

3. The method according to claim 1 comprising a daily administration of a low-dose cytokine.

4. The method of claim 1, wherein the dose of IFN-α is in the range of from 1-10 MIU three times a week.

5. The method of claim 1 wherein the cytokine is administered in a constant dose during the treatment.

6. The method of claim 1 wherein the IFN-α is administered subcutaneously.

7. The method of claim 1 wherein the antitumor antibody G250 is administered in intervals of from 5-20 days.

8. The method of claim 2 wherein the first treatment stage comprises 5-20 days.

9. The method of claim 2 wherein the second treatment stage comprises 50-200 days.

10. A method for the treatment of renal cell cancer comprising co-administering an anti-tumor antibody G250 or an antigen binding fragment thereof and a cytokine IFN-α as the only active ingredients to a subject in need thereof, wherein the cytokine is administered continuously or repeatedly in a low-dose form, wherein the low-dose cytokine comprises a dose which is pharmaceutically effective in the absence of NIC CTC toxicity grade 3 or higher.

11. A method for the treatment of renal cell cancer consisting essentially of co-administering an anti-tumor antibody directed against the MN antigen, wherein said antitumor antibody is a chimeric or humanized G250 antibody or an antigen binding fragment thereof and a cytokine to a subject in need thereof, wherein the cytokine is IFN-α and is administered continuously or repeatedly in a low-dose form, wherein the low-dose cytokine comprises a dose which is pharmaceutically effective in the absence of NIC CTC toxicity grade 3 or higher and wherein said IFN-α is the only cytokine which is administered.

* * * * *

UNITED STATES PATENT AND TRADEMARK OFFICE
CERTIFICATE OF CORRECTION

PATENT NO. : 7,632,496 B2      Page 1 of 1
APPLICATION NO. : 10/517338
DATED : December 15, 2009
INVENTOR(S) : Warnaar et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 94 days.

Signed and Sealed this

Second Day of November, 2010

David J. Kappos
*Director of the United States Patent and Trademark Office*